United States Patent
Krauss

(10) Patent No.: US 7,936,909 B2
(45) Date of Patent: May 3, 2011

(54) METHOD AND DEVICE FOR DETECTING CHEMICAL ANOMALIES AND/OR SALIENT FEATURES IN SOFT TISSUE OF AN OBJECT AREA

(75) Inventor: Bernhard Krauss, Burgthann (DE)

(73) Assignee: Siemens Aktiengesellschaft, Munich (DE)

( * ) Notice: Subject to any disclaimer, the term of this patent is extended or adjusted under 35 U.S.C. 154(b) by 978 days.

(21) Appl. No.: 11/730,272

(22) Filed: Mar. 30, 2007

(65) Prior Publication Data
US 2008/0037699 A1 Feb. 14, 2008

(30) Foreign Application Priority Data
Mar. 31, 2006 (DE) .......................... 10 2006 015 452

(51) Int. Cl.
*A61B 6/00* (2006.01)
*G06K 9/00* (2006.01)
*A61B 5/05* (2006.01)

(52) U.S. Cl. ........ 382/128; 382/129; 382/130; 382/131; 382/132; 378/4; 600/425

(58) Field of Classification Search .......... 382/128–132; 378/4; 600/425
See application file for complete search history.

(56) References Cited

U.S. PATENT DOCUMENTS

| 6,597,759 B2 * | 7/2003 | Mazess et al. ................. 378/53 |
| 2004/0184574 A1 | 9/2004 | Wu et al. |
| 2006/0251209 A1 * | 11/2006 | Tkaczyk et al. ................. 378/5 |

FOREIGN PATENT DOCUMENTS
WO WO 2006/121673 A1 11/2006

OTHER PUBLICATIONS

Mohammad R. ("Accurate determination of chemical composition of urinary calculi by spiral computerized tomography" the journal of urology, vol. 159, pp. 673-675, Mar. 1998, USA).*
Chee et al. ("Helical CT of Urinary Calculi: Effect of Stone composition, stone size, and scan collimation", Journal to American Roentgen Ray Society, ARJ:175, Aug. 2000).*

* cited by examiner

*Primary Examiner* — Anand Bhatnagar
*Assistant Examiner* — Amara Abdi
(74) *Attorney, Agent, or Firm* — Harness, Dickey & Pierce, P.L.C.

(57) ABSTRACT

At least one embodiment of the present application relates to a method and/or a device for automatically detecting chemical anomalies and/or salient features in soft tissue of an object area. In at least one embodiment of the method, two image data records of two computed tomography pictures of the object are provided which are recorded in the context of a different spectral distribution of the X-radiation. The following steps are carried out for each voxel of at least one interesting slice whose X-ray attenuation values are characteristic of soft tissue. Firstly, two X-ray attenuation values of the voxel, or two averaged X-ray attenuation values of the environment of the voxel are used to determine a data point of the voxel in a diagram in which the X-ray attenuation values are plotted against one another in the context of the two spectral distributions of the X-radiation. A perpendicular distance of the data point from a connecting straight line that connects prescribed data points for pure fat and for pure soft tissue in the diagram is then calculated. Finally, the voxel is marked and displayed with highlighting when its distance exceeds a prescribed threshold value for the distance. In at least one embodiment, at least one of the proposed method and the associated device enable chemical anomalies to be automatically detected on the basis of computed tomography.

20 Claims, 2 Drawing Sheets

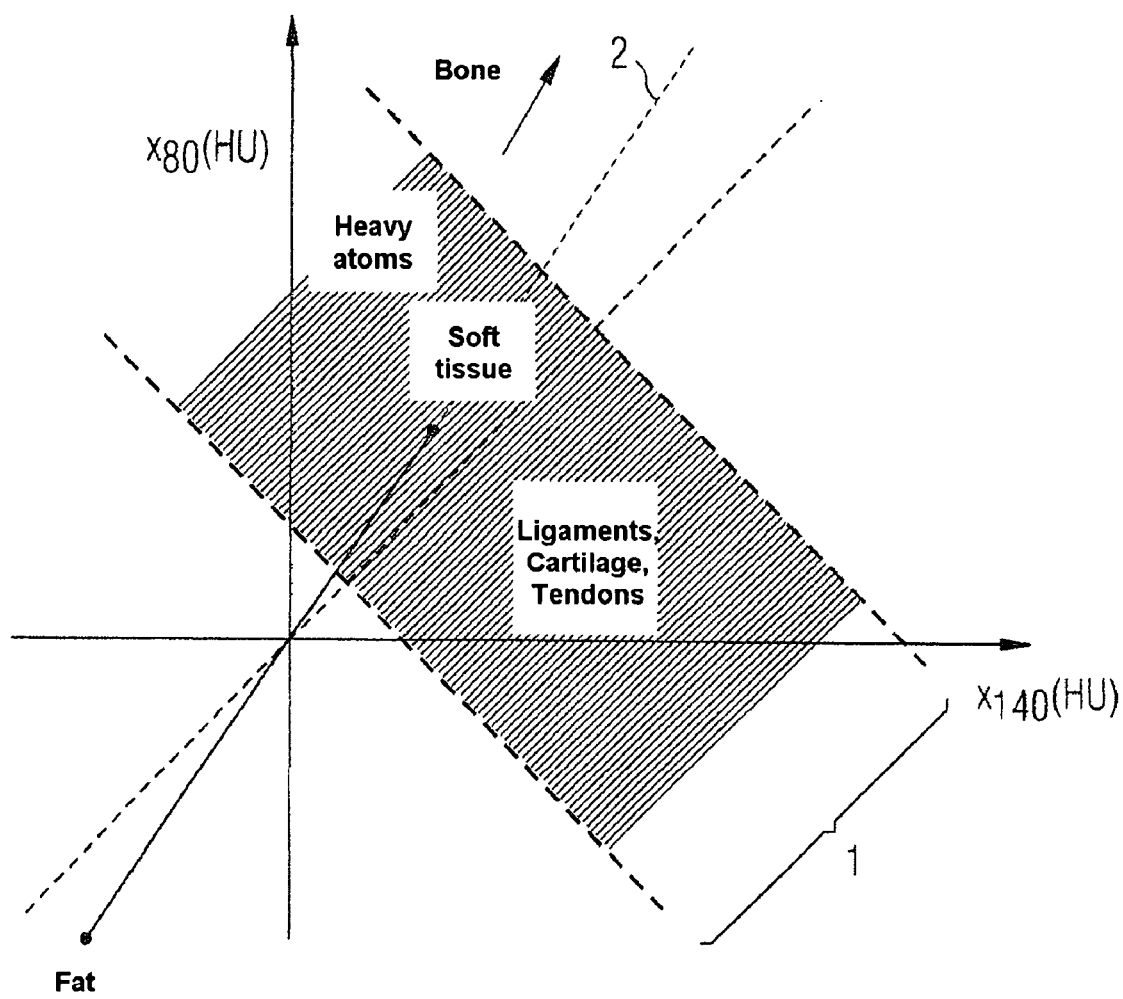

METHOD AND DEVICE FOR DETECTING CHEMICAL ANOMALIES AND/OR SALIENT FEATURES IN SOFT TISSUE OF AN OBJECT AREA

PRIORITY STATEMENT

The present application hereby claims priority under 35 U.S.C. §119 on German patent application numbers DE 10 2006 015 452.5 filed Mar. 31, 2006, the entire contents of each of which is hereby incorporated herein by reference.

FIELD

Embodiments of the present invention generally relate to a method and/or a device for automatically detecting chemical anomalies and/or salient features in soft tissue of an object area. For example, in an embodiment of the method, in it may relate to one in which two computed tomography pictures of an object area are recorded in the context of a different spectral distribution of the X-radiation, and there are reconstructed from raw data of the two computed tomography pictures two image data records of the object area that include X-ray attenuation values of voxels on the object area in the context of the respective spectral distribution of the X-radiation.

BACKGROUND

The detection of a particular chemical composition of soft tissue in the human or animal body is required for many medical applications. These applications include, for example, the exact localization of ligaments and tendons, for example in the case of bone fractures, the identification of an incipient calcification of ligaments, the estimation of amount of cartilage present in joints, or the distinguishing of healthy body tissues and hematomas in a certain time interval after the emergence of the hematoma.

To date, corresponding chemical anomalies and/or salient features in soft tissue have chiefly been identified by using magnetic resonance tomography. However, this requires the use of a magnetic resonance tomograph that is not available straight away in every case.

SUMMARY

At least one embodiment of the present invention provides a method and/or a device for detecting or for identifying chemical anomalies and/or salient features in soft tissue of an object area that enable automatic detection without the use of a magnetic resonance tomograph.

In an embodiment of the present method, two computed tomography pictures of the object area are recorded in the context of a different spectral distribution of the X-radiation, and there are reconstructed from raw data of the two computed tomography pictures two image data records of the object area that include X-ray attenuation values of voxels on the object area in the context of the respective spectral distribution of the X-radiation. X-ray attenuation values can be understood here both as the attenuation coefficients $\mu$ and as values derived therefrom, such as the CT value. Two computed tomography pictures are recorded by using a multi-energy computer tomograph, preferably a so-called dual energy computer tomograph, with the aid of which it is possible simultaneously or at least almost simultaneously, to record two computed tomography pictures with a different spectral distribution of the X-radiation or different X-ray energy.

Different techniques for generating two computed tomography pictures with a different spectral distribution of the X-radiation are fundamentally known to the specialist. It is possible for this end, for example, to make use of a number of X-ray sources with a different tube voltage, different detectors of different spectral sensitivity, different filters in front of the X-ray sources and/or X-ray detectors, or else of a combination of said techniques.

In the case of at least one embodiment of the present method, mean values are then formed from the respective two X-ray attenuation values of each voxel of at least one interesting slice of the object area, and at least the following steps are carried out for at least a portion of the voxels whose mean values lie inside a prescribed value range that is characteristic of soft tissue. Firstly, a data point of the voxel is determined in a diagram in which the X-ray attenuation values are plotted against one another in the context of the two different X-ray energies. In this case, the X-ray attenuation values are plotted on one of the two axes of the diagram for one X-ray energy, and the X-ray attenuation values are plotted on the second axis for the other X-ray energy.

In one refinement of an embodiment of the present invention, the data point is composed of a voxel from two X-ray attenuation values that are assigned to this in the two image data records. In a second alternative embodiment of the method, X-ray attenuation values averaged for each of the voxels are calculated that are yielded separately for each image data record from the X-ray attenuation values of selected voxels from the environment of the relevant voxel. In each case, there is obtained here for each relevant voxel a data point that is composed of an attenuation value in the context of one of the two spectral distributions or X-ray energies, and an attenuation value in the content of the other two spectral distributions or X-ray energies.

After the determination of the data point in the diagram, a perpendicular distance u of the data point of the voxel is calculated from a connecting straight line that connects predetermined data points for pure fat and for pure soft tissue in this diagram. The magnitude of this distance u constitutes a measure of probability that a chemical anomaly is present. The basis for this step is a 3-material decomposition in the case of which the respective voxel is interpreted as a mixture of the base materials of soft tissue and fat with a further unknown substance. All the voxels that include a mixture of soft tissue and fat (and water) lie in the diagram on the straight line between the pure substances of soft tissue and fat. Data points that lie further away from this straight line indicate anomalies or salient features. This relates, for example, to soft tissues in which heavy atoms such as, for example, iron are stored, or tissues that are rich in carbon such as for example, connective tissues.

In the case of at least one embodiment of the present method, voxels whose distance u exceeds a prescribed threshold value of the distance are now marked and displayed with suitable highlighting. This can be done by isolated display of the marked voxels, or else by displaying these voxels with colored highlighting in an image of the object area.

The viewer can then detect at once in the CT images the location and the extent of corresponding chemical anomalies and/or salient features in the soft tissue.

At least one embodiment of the present method and the associated device therefore enable the detection or the identification of chemical anomalies and/or salient features in soft tissue even without the use of magnetic resonance tomography. The diagnostic image material is also provided in this case substantially more quickly than is the case with the processing of magnetic resonance tomography pictures. A further advantage of at least one embodiment of the present method and of the associated device resides in that it is necessary for a CT scan to be carried out anyway in many cases, for example with bone fractures, and thus there is no need for additional investigation using another imaging unit such as the magnetic resonance tomograph.

Examples of chemical anomalies and/or salient features in soft tissue that can be detected with the aid of at least one embodiment of the present method and the associated device are tissue parts that contain an unusual amount of carbon such as, for example, ligaments, tendons or cartilage. Further examples are tissue regions containing concentrations of heavy atoms (for example iron) such as can occur temporarily, for example in the case of a hematoma, or permanently, for example in the case of calcifications. The medical applications in this case cover the exemplary applications already mentioned in the introduction, but are not limited thereto.

In an advantageous development of at least one embodiment of the method, use is made as data points of the respective voxel not of the pure X-ray attenuation values of this voxel in the context of the different spectral distributions, but of averaged X-ray attenuation values that are yielded from X-ray attenuation values of a few selected voxels inside a volume area around the relative voxel, denoted below as central voxel. In this case, a three dimensional volume area, preferably a spherical volume, having a prescribed extent around the central voxel is formed before the determination of the respective data point. All the voxels whose X-ray attenuation values fulfill a prescribed criterion that is characteristic of soft tissue are selected inside this volume area. An averaged attenuation value of the selected voxels is calculated separately for each image data record such that two averaged X-ray attenuation values are obtained over all, that is to say one averaged X-ray attenuation value for each X-ray energy. These two averaged X-ray attenuation values are then used to form the data point of the central voxel, from which the perpendicular distance from the connecting straight line is subsequently calculated. This step enables a systematic selection of neighboring voxels, which probably have the same composition. No blind averaging is performed over a large space. Cartilage and bone can thereby be distinguished at short distances, and ligaments and soft tissue at long distances.

In at least one embodiment of a refinement of the method, the steps of determining the data point and of calculating the distance u from the connecting straight line are not carried out for all the voxels whose mean values lie inside the prescribed value range, but only for a number of these voxels that are defined in the following way. To this end, the number of selected voxels is determined in the three dimensional volume area, around the respective central voxel, whose X-ray attenuation values fulfill the prescribed criterion. If this number lies above a prescribed threshold value for the number of the selected voxels, the data point of this central voxel is determined from the averaged X-ray attenuation values, as just described, and the distance of the data point thus obtained from the connecting straight line is calculated. If, however, the number of the selected voxels lies below the threshold value, no further calculation kind is carried out for this central voxel. It is then assumed that this voxel does not constitute a site with an anomaly and/or salient feature in the object area investigated.

In one refinement of at least one embodiment of the present method, it is possible to use as criterion in accordance with which the voxels are selected inside the three-dimensional volume area the fact that the mean value of the two X-ray attenuation values of the respective voxel must lie inside the value range for soft tissue.

However, it is preferred in the case of this criterion for the basis to be not the mean value, but a combined X-ray attenuation value that represents a weighted value $x_m$ dependent on the image noise ratio q between the images of the two computed tomography pictures, and is calculated using the following rule:

$$x_m = \frac{x_1 - m \cdot x_2}{1 - m}, \text{ in which } m = -\frac{q^2}{r} \text{ and } r = \frac{x_{g,1} - x_{f,1}}{x_{g,2} - x_{f,2}}.$$

$x_1$ and $x_2$ represents the X-ray attenuation values, for example HU values (HU: Hounsfield Units), in the case of the two different X-ray energies. $x_f$ corresponds to the X-ray attenuation value for pure fat for the respective X-ray energy, and $x_g$ to the X-ray attenuation value of pure soft tissue for the respective X-ray energy. q represents the ratio of the image noise of the images of the two computed tomography pictures. This image noise ratio q is yielded from $q=dx_1/dx_2$, where $dx_1$ and $dx_2$ represent the statistical errors, that is to say the standard deviation, of the X-ray attenuation values $x_1$ and $x_2$. The voxels are then selected inside the three-dimensional volume area on the basis of the combined X-ray attenuation value $x_m$. All the voxels for which this combined X-ray attenuation value $x_m$ lies inside the prescribed value range that is characteristic of soft tissue are selected.

This mode of procedure based on the combined X-ray attenuation value that represents a weighted mean value dependent on the image noise ratio q substantially reduces the risk of an erroneous selection, caused by the image noise, in the vicinity of the interval limits, and so a more reliable result is attained. The ratio q of the image noise of the two image data records that is required for this purpose can already be known for the computed tomography installation being used, or be determined in advance from the two image data records, or else other image data records, for example topograms recorded in advance.

At least one embodiment of the device for automatically detecting chemical anomalies and/or salient features in soft tissue of an object area comprises, in addition to a memory unit for the two image data records as main constituent, a determination module that carries out the calculations and determinations in accordance with the previously described method and, if appropriate, the individual developments of this method. The determination module is in this case preferably implemented in the image computer of the computed tomography installation that can supply the raw data for the two computed tomography pictures in the context of a different spectral distribution of the X-radiation. In this case, the device also comprises an image reconstruction module that reconstructs the two image data records of the object area from the raw data of the two computed tomography pictures.

In one refinement of at least one embodiment, the device can, however, also comprise only the determination module with the memory unit, and an interface via which already reconstructed image data records from the two computed tomography pictures are received. The determination module is preferably connected to an image display module via which the voxels representing anomalies and/or salient features in soft tissue can be displayed on a corresponding image display unit.

BRIEF DESCRIPTION OF THE DRAWINGS

The present method is explained once again briefly below with the aid of an example embodiment in conjunction with the drawings, in which:

FIG. 2 shows an example of an HU value diagram for determining the perpendicular distance of the data point from the connecting straight line.

DETAILED DESCRIPTION OF THE EXAMPLE EMBODIMENTS

Figure 1:
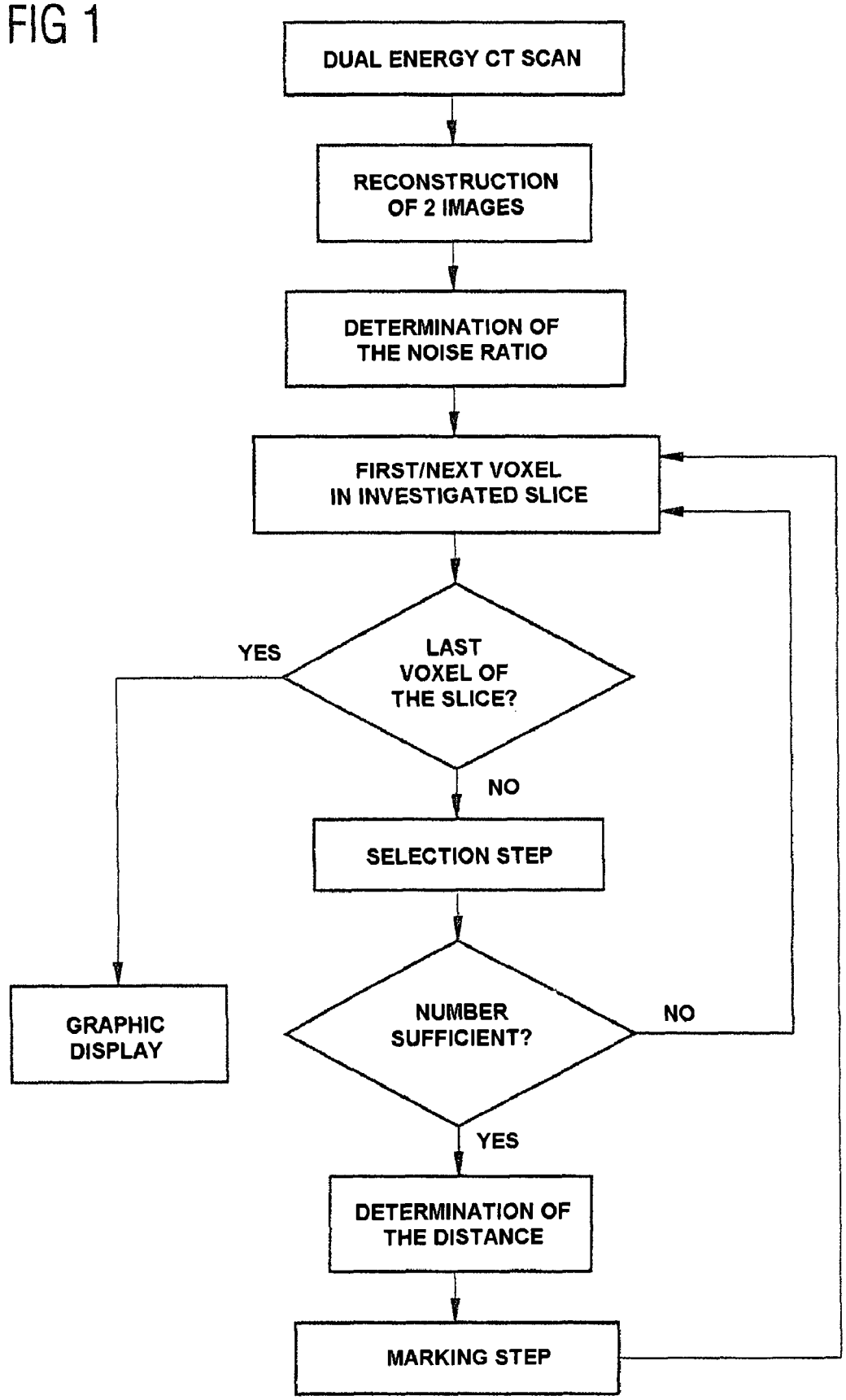
FIG. 1 shows an example of a method cycle in carrying out an embodiment of the present method.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

In the present example embodiment, a dual energy computer tomograph is used to carry out a dual energy CT scan of the object, in which raw data are simultaneously obtained in the context of two different X-ray energies. These different X-ray energies are obtained by way of a different tube voltage of the X-ray tubes used, 80 kV and 140 kV, in the present example. Two CT images are reconstructed independently of one another from the raw data via a known reconstruction algorithm. Each of the two image data records obtained in this case includes for each voxel of the investigation volume, a corresponding HU value for the respective X-ray energy.

Irrespective of the data recording and the computer tomograph used, it should be ensured in this case that the HU values for the body materials to be differentiated are to some extent stable when they occur or are positioned at different sites inside the object being investigated. This is, however, the case for most commercially available computer tomographs.

In the present example embodiment, only an axial slice is considered during preprocessing. If the ratio q of the image noise between the image for 80 kV and the image for 140 kV is not known for this slice, this ratio q can, for example be determined approximately from the object diameter or the measured noise of the HU values of air. It is possible to this end, for example, to calculate for both tube voltages the mean noise for all the pixels of the slice below a certain threshold, for example, below −950 HU, in the upper half of the image, and to form the ratio subsequently. It is likewise possible to determine this ratio from a previously recorded topogram, for example.

In addition to the slice being investigated, a number of voxel slices above and below it are also required for the main portion of the processing. The term "combined HU value" used below denotes the weighted mean value $x_m$, dependent on the image noise ratio, of the HU values for 80 kV and 140 kV ($x_{80}$ and $x_{140}$) respectively. This can be calculated from the ratio q and the HU values of tissue (80 kV: $x_{g,\,80}$; 140 kV: $x_{g,\,140}$) and fat (80 kV: $x_{f,80}$; 140 kV: $x_{f,140}$):

$$x_m = \frac{x_{80} - m \cdot x_{140}}{1-m}, \text{ in which } m = -\frac{q^2}{r} \text{ and } r = \frac{x_{g,80} - x_{f,80}}{x_{g,140} - x_{f,140}}.$$

By contrast therewith the term "averaged HU value" is calculated as the arithmetic mean from the HU values for 80 kV and 140 kV, $x_{80}$ and $x_{140}$.

The following three steps are then carried out (cf. FIG. 1) for each voxel in the slice being investigated, given that the mean HU value of this voxel lies inside a typical interval for soft tissue:

1. Selection step: a three-dimensional spherical environment of the investigated voxel is considered. Use is made only of voxels whose combined HU value lies inside the interval for soft tissue. In this way, all the neighboring voxels possibly having the same chemical composition are firstly selected. If the combined HU value lies inside the soft tissue interval for less than $n_{min}$ voxels in the volume considered, the following steps are omitted and no material assignment is made. Otherwise, a mean HU value $x_{80}$ for 80 kV is calculated for this selected voxel, and a mean HU value $x_{140}$ is calculated for 140 kV, this being done in each case by averaging over the HU values of all the selected voxels. A radius of 6 voxels can be adopted as an example of the spherical environment, and a value of 40 voxels can be adopted as an example of the threshold value $n_{min}$. Of course, these values can, however, also be selected otherwise, depending on the application and image quality.

2. 3-material decomposition: the selected voxels are interpreted as a mixture of the base materials of soft tissue, fat and a further unknown substance. All the volumes that contain a mixture of soft tissue and fat (and water) lie in a diagram, in which $x_{80}$ is plotted against $x_{140}$, on a straight line 1 between the pure substances of soft tissue and fat. FIG. 2 shows this HU value diagram, there likewise being depicted the HU interval 1 inside which the averaged HU values and the combined HU values of the respective voxels must lie, that is to say inside which the presence of soft tissue is probable. Also depicted in the figure is the connecting straight line 2 between pure soft tissue and pure fat. Data points that lie far removed from this straight line 2 indicate chemical anomalies. Lying above the straight lines are soft tissues that store heavy atoms. Below the straight line lie materials that are rich in carbon such as, for example, connective tissues. Connective tissue that has stored sufficient lime also lies above the straight lines.

3. Determination of a measure of probability: the probability that a chemical anomaly is present is scaled on the assumption that the statistical noise of the 80 kV image and of the 140 kV image is virtually constant with the distance u from said straight line. The probability of an anomaly is high above a threshold that is determined as a rule by statistical and systematic errors. The perpendicular distance u from the straight line 2 is therefore determined for each data point considered.

The following scaling has additionally proved itself for cartilage and connective tissues (below the straight lines):

$$y=(x_1 \cdot u)/S_u.$$

Here, $x_1$ denotes the averaged local HU value of the voxel considered, and $s_u$ denotes an arbitrary scale factor that can amount to a few HU. This weighted variable y indicates local changes in density such as for example, cartilage with relatively high spatial resolution.

By contrast $x_1$ is immaterial for the display of hematomas (above the straight lines). It is preferred in this case to make use of $y=u/s_u$. This calculation can have the disturbing effect of throwing up mixtures of bone and bone marrow. In order to prevent this, very high values of y can also be masked out by prescribing an appropriate threshold value, that is to say for example be set to zero.

Once the image stack or the three-dimensional image data records, are completely processed, the y map thus prepared can be used to mark the chemical anomaly in color, or to isolate anomalous regions chemically.

The following parameters are required in this example to carry out an embodiment of the method:

| Parameter | Meaning |
|---|---|
| $x_{min}$ | Lower threshold (HU) for cartilage/soft tissue voxels |
| xmax | Upper threshold (HU) for cartilage/soft tissue voxels |
| s | Radius of the volume considered |
| $n_{min}$ | Minimum number of selected voxels |
| $x_{g, 80}$ | HU value of soft tissue for 80 kV |
| $x_{g, 140}$ | HU value of soft tissue for 140 kV |
| $x_{f, 80}$ | HU value of fat for 80 kV |
| $x_{f, 140}$ | HU value of fat for 140 kV |
| $S_u$ | Scaling of the variable y |

In the case of an embodiment of the present method and an embodiment of the associated device, 3-material decomposition chiefly enables the distinguishing of "normal" soft tissue, which consists of soft tissue, fat or water, and all other tissues without the application of complicated distinguishing criteria. The measure of probability has the effect that statistical fluctuations are displayed only weakly, while reliable regions are clearly marked.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method comprising:
automatically detecting at least one of chemical anomalies and salient features in soft tissue of an object area,
wherein two computed tomography pictures of the object area are recorded in a context of a different spectral distribution of X-radiation,
wherein two image data records of the object area are reconstructed from raw data of the two computed tomography pictures, the two image data records including X-ray attenuation values of voxels on the object area in the context of a respective spectral distribution of the X-radiation, and
wherein, for at least a portion of voxels of at least one slice of the object area whose mean value from two X-ray attenuation values of the two image data records lies within a prescribed value range, the automatically detecting includes,
determining a data point of the voxel in a diagram from at least one of the two X-ray attenuation values of the voxel and two averaged X-ray attenuation values that are obtained by averaging X-ray attenuation values of voxels inside a prescribed volume around the voxel in the respective image data record, the diagram including the two X-ray attenuation values plotted against one another in the context of two spectral distributions of the X-radiation,
calculating a perpendicular distance of the data point of the voxel from a connecting straight line that connects prescribed data points for pure fat and for pure soft tissue in the diagram, and
marking and highlighting the voxel when the calculated distance exceeds a prescribed value for the distance.

2. The method as claimed in claim 1, wherein, for each voxel whose mean value from the two assigned x-ray attenuation values lies inside the prescribed value range that is characteristic of soft tissue, firstly a three-dimensional volume area with a prescribed extent around the voxel is prescribed there are selected inside the volume area all the voxels whose X-ray attenuation values fulfill a prescribed criterion that is characteristic of soft tissue, and an averaged attenuation value of the selected voxels is calculated separately for each image data record in order to determine from the two averaged X-ray attenuation values the data point of the voxel from which the perpendicular distance from the connecting straight line is subsequently calculated.

3. The method as claimed in claim 1, wherein, for each voxel whose mean value from the two assigned X-ray attenuation values lies inside the prescribed value range that is characteristic of soft tissue, firstly a three dimensional volume area with a prescribed extent around the voxel is prescribed, there are selected inside the volume area all the voxels whose X-ray attenuation values fulfill a prescribed criterion that is characteristic of soft tissue, a number of selected voxels in the volume area is determined and is compared with a prescribed threshold value for the number, and an averaged attenuation value of the selected voxels is calculated separately for each image data record in order to determine from the two averaged X-ray attenuation values the data point of the voxel from which the perpendicular distance from the connecting straight line is subsequently calculated, the calculation of the averaged X-ray attenuation values, and the further steps of patent claim 1 being carried out only in the case of voxels where the number of the selected voxels exceeds the prescribed threshold value for the number.

4. The method as claimed in claim 2, wherein the definition of the prescribed criterion is that the mean value of the two X-ray attenuation values of the voxel lies inside the prescribed value range that is characteristic of soft tissue.

5. The method as claimed in claim 2, wherein the definition of the prescribed criterion is that a combined attenuation value $x_m$ of the voxel lies inside a prescribed value range that is characteristic of soft tissue, the combined attenuation value being obtained from the following calculation rule:

$$x_m = \frac{x_1 - m \cdot x_2}{1-m}, \text{ in which } m = -\frac{q^2}{r} \text{ and } r = \frac{x_{g,1} - x_{f,1}}{x_{g,2} - x_{f,2}},$$

$x_1$ and $x_2$ representing the two X-ray attenuation values of the voxel in the context of the two different spectral distributions of the X-radiation, $x_f$ representing the attenuation value of pure fat in the context of the respective spectral distribution, $x_g$ representing the attenuation value of pure soft tissue in the context of the respective spectral distribution, and q representing the ratio of the image noise of the images of the two image data records.

6. The method as claimed in claim 5, wherein the ratio of the image noise is determined in a preprocessing step at least one of from the two image data records and from topograms recorded in advance.

7. The method as claimed in claim 1, wherein the prescribed threshold value for the distance is scaled using the mean value of the two X-ray attenuation values of the voxel for a detection of at least one of cartilage and connective tissue.

8. The method as claimed in claim 1, wherein the prescribed threshold value for the distance is a constant value for a detection of hematomas.

9. The method as claimed in claim 1, wherein the highlighted display is performed at least one of by isolated display of the voxels whose distance exceeds the prescribed threshold value for the distance, and by colored display of these voxels in an image of the object area.

10. A device for automatically detecting at least one of chemical anomalies and salient features in soft tissue of an object area, the device comprising:
    a memory unit to store two image data records of the object area obtained from two computed tomography pictures of the object area in the context of a different spectral distribution of the X-radiation, and including X-ray attenuation values of voxels of the object area in the context of the respective spectral distribution of the X-radiation; and
    a determination module, for each voxel of at least one interesting slice of the object area, to determine a mean value from the two assigned X-ray attenuation values of the two image data records, and to carry out at least the following for each voxel whose mean value lies inside a prescribed value range that is characteristic of soft tissue,
        determining a data point of the voxel in a diagram, in which X-ray attenuation values are plotted against one another in the context of two spectral distributions of the X-radiation, at least one of from the two X-ray attenuation values of the voxel or from two averaged X-ray attenuation values obtained by averaging the X-ray attenuation values of voxels inside a prescribed volume around the voxel in the respective image data record,
        calculating a perpendicular distance of the data point of the voxel from a connecting straight line that connects prescribed data points for pure fat and for pure soft tissue in the diagram, and
        marking and highlighting the voxel when the calculated distance exceeds a prescribed threshold value for the distance.

11. The device as claimed in claim 10, wherein the determination module is further used, for each voxel whose mean value from the two assigned X-ray attenuation values lies inside the prescribed value range that is characteristic of soft tissue, to firstly define a three-dimensional volume area with a prescribed extent around the voxel, to select inside the volume area all the voxels whose X-ray attenuation values fulfill a prescribed criterion that is characteristic of soft tissue, and to calculate an averaged attenuation value for the selected voxels separately for each image data record, to determine from the two averaged X-ray attenuation values the data point of the voxel from which the perpendicular distance from the connecting straight line is subsequently calculated.

12. The device as claimed in claim 10, wherein the determination module is further used, for each voxel whose mean value from the two assigned X-ray attenuation values lies inside the prescribed value range that is characteristic of soft tissue, to firstly define a three-dimensional volume area with a prescribed extent around the voxel, to select inside the volume area all the voxels whose X-ray attenuation values fulfill a prescribed criterion that is characteristic of soft tissue, to determine a number of the selected voxels in the volume region and compares it with a prescribed threshold value for the number, and to calculate an averaged attenuation value of the selected voxels separately for each image data record, in order to determine from the two averaged X-ray attenuation values the data point of the voxel from which the perpendicular distance from the connecting straight line is subsequently calculated, the calculation of the averaged X-ray attenuation values being carried out only in the case of voxels where the number of the selected voxels exceeds the prescribed threshold value for the number.

13. The device as claimed in claim 11, wherein the definition of the prescribed criterion is that the mean value of the two X-ray attenuation values of the voxel lies inside the prescribed value range that is characteristic of soft tissue.

14. The device as claimed in claim 11, wherein the definition of the prescribed criterion is that a combined attenuation value $x_m$ of the voxel lies inside a prescribed value range that is characteristic of soft tissue, the determination module being used to obtain the combined attenuation value from the following calculation rule:

$$x_m = \frac{x_1 - m \cdot x_2}{1-m}, \text{ in which } m = -\frac{q^2}{r} \text{ and } r = \frac{x_{g,1} - x_{f,1}}{x_{g,2} - x_{f,2}},$$

$x_1$ and $x_2$ representing the two X-ray attenuation values of the voxel in the context of the two different spectral distributions of the X-radiation, $x_f$ representing the attenuation value of pure fat in the context of the respective spectral distribution, $x_g$ representing the attenuation value of pure soft tissue in the context of the respective spectral distributions, and q representing the ratio of the image noise of the images of the two image data records.

15. The method as claimed in claim 3, wherein the definition of the prescribed criterion is that the mean value of the two X-ray attenuation values of the voxel lies inside the prescribed value range that is characteristic of soft tissue.

16. The method as claimed in claim 3, wherein the definition of the prescribed criterion is that a combined attenuation value $x_m$ of the voxel lies inside a prescribed value range that is characteristic of soft tissue, the combined attenuation value being obtained from the following calculation rule:

$$x_m = \frac{x_1 - m \cdot x_2}{1-m}, \text{ in which } m = -\frac{q^2}{r} \text{ and } r = \frac{x_{g,1} - x_{f,1}}{x_{g,2} - x_{f,2}},$$

$x_1$ and $x_2$ representing the two X-ray attenuation values of the voxel in the context of the two different spectral distributions of the X-radiation, $x_f$ representing the attenuation value of pure fat in the context of the respective spectral distribution, $x_g$ representing the attenuation value of pure soft tissue in the context of the respective spectral distribution, and q representing the ratio of the image noise of the images of the two image data records.

17. The device as claimed in claim 12, wherein the definition of the prescribed criterion is that the mean value of the two X-ray attenuation values of the voxel lies inside the prescribed value range that is characteristic of soft tissue.

18. The device as claimed in claim 12, wherein the definition of the prescribed criterion is that a combined attenuation value $x_m$ of the voxel lies inside a prescribed value range that is characteristic of soft tissue, the determination module being used to obtain the combined attenuation value from the following calculation rule:

$$x_m = \frac{x_1 - m \cdot x_2}{1 - m}, \text{ in which } m = -\frac{q^2}{r} \text{ and } r = \frac{x_{g,1} - x_{f,1}}{x_{g,2} - x_{f,2}},$$

$x_1$ and $x_2$ representing the two X-ray attenuation values of the voxel in the context of the two different spectral distributions of the X-radiation, $x_f$ representing the attenuation value of pure fat in the context of the respective spectral distribution, $x_g$ representing the attenuation value of pure soft tissue in the context of the respective spectral distributions, and q representing the ratio of the image noise of the images of the two image data records.

19. A device for automatically detecting at least one of chemical anomalies and salient features in soft tissue of an object area, the device comprising:

means for storing two image data records of the object area obtained from two computed tomography pictures of the object area in the context of a different spectral distribution of the X-radiation, and including X-ray attenuation values of voxels of the object area in the context of the respective spectral distribution of the X-radiation; and means, for each voxel of at least one interesting slice of the object area, for determining a mean value from the two assigned X-ray attenuation values of the two image data records, and to carry out at least the following for each voxel whose mean value lies inside a prescribed value range that is characteristic of soft tissue, determining a data point of the voxel in a diagram, in which X-ray attenuation values are plotted against one another in the context of two spectral distributions of the X-radiation, at least one of from the two X-ray attenuation values of the voxel or from two averaged X-ray attenuation values obtained by averaging the X-ray attenuation values of voxels inside a prescribed volume around the voxel in the respective image data record, calculating a perpendicular distance of the data point of the voxel from a connecting straight line that connects prescribed data points for pure fat and for pure soft tissue in the diagram, and marking and highlighting the voxel when the calculated distance exceeds a prescribed threshold value for the distance.

20. The device as claimed in claim 19, wherein the means for determining is further for, for each voxel whose mean value from the two assigned X-ray attenuation values lies inside the prescribed value range that is characteristic of soft tissue, firstly defining a three-dimensional volume area with a prescribed extent around the voxel, for selecting inside the volume area all the voxels whose X-ray attenuation values fulfill a prescribed criterion that is characteristic of soft tissue, and for calculating an averaged attenuation value for the selected voxels separately for each image data record, to determine from the two averaged X-ray attenuation values the data point of the voxel from which the perpendicular distance from the connecting straight line is subsequently calculated.

* * * * *